United States Patent
Zapletal

[11] Patent Number: 6,135,973
[45] Date of Patent: Oct. 24, 2000

[54] NECK SUPPORTING DEVICE

[75] Inventor: Jiri Zapletal, Driebergen, Netherlands

[73] Assignee: World Health Club S.A., Luxembourg

[21] Appl. No.: 09/290,718

[22] Filed: Apr. 12, 1999

Related U.S. Application Data

[63] Continuation-in-part of application No. 09/104,502, Jun. 25, 1998.

[51] Int. Cl.[7] .................................................. A61F 5/00
[52] U.S. Cl. ........................ 602/18; 602/19; 128/DIG. 23
[58] Field of Search ................................. 128/845, 846, 128/DIG. 23, 869, 875, 876; 602/5, 17, 18

[56] References Cited

U.S. PATENT DOCUMENTS

| | | | |
|---|---|---|---|
| 1,510,187 | 9/1924 | Martin | 128/DIG. 23 |
| 2,223,276 | 11/1940 | Ward | 602/18 |
| 3,397,688 | 8/1968 | Gottfried | 602/18 |
| 4,034,747 | 7/1977 | Leroy | 128/DIG. 23 |
| 4,141,368 | 2/1979 | Meyer | 602/18 |
| 4,757,554 | 7/1988 | Blair | 602/18 |
| 5,056,508 | 10/1991 | Brunell | 602/18 |
| 5,409,450 | 4/1995 | Donelson | 602/18 |

*Primary Examiner*—Michael A. Brown
*Attorney, Agent, or Firm*—Quarles & Brady LLP

[57] ABSTRACT

A neck supporting device comprising a neck support for supporting the back of the neck and the back lower part of the head of a wearer, and two connecting straps for, each from a respective end of the neck support, connecting the neck support to a body harness such that, in use, the connecting straps are directed to the lower torso of the wearer. The neck support includes a semi-rigid member having a curvature adapted to the curvature of the back of the neck and the back lower part of the head when the head is positioned in a non-tilted position with respect to the wearer's torso. The neck supporting device may comprise a waist belt as the body harness or may be adapted for fastening to a car safety belt as the body harness.

32 Claims, 3 Drawing Sheets

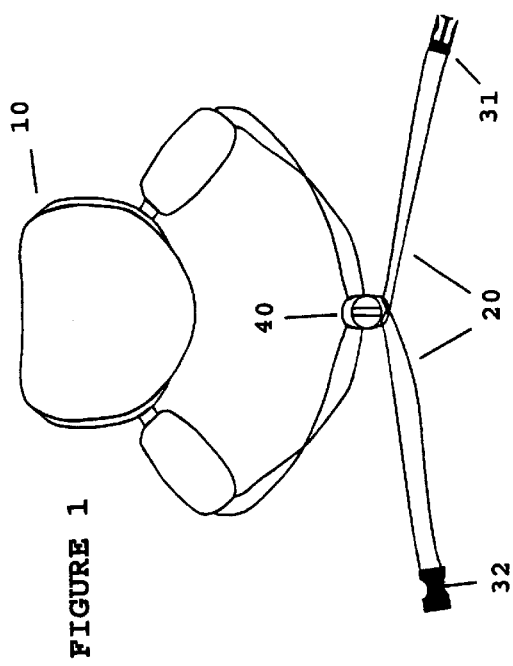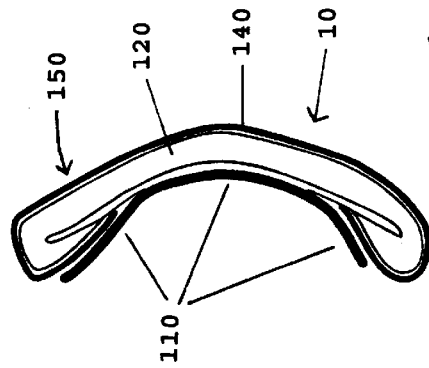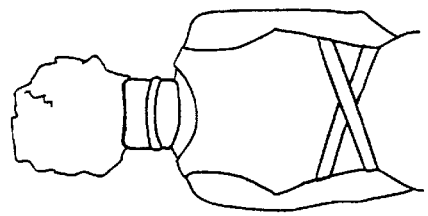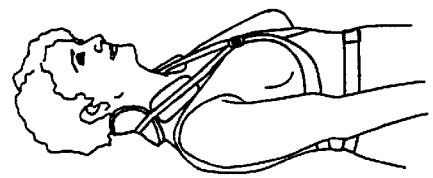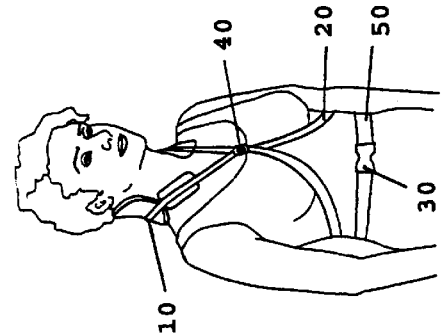

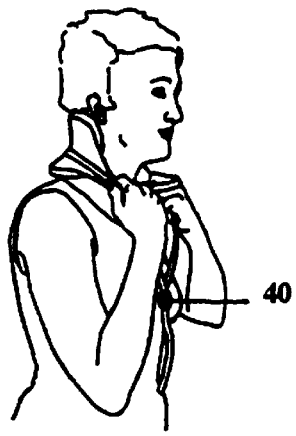 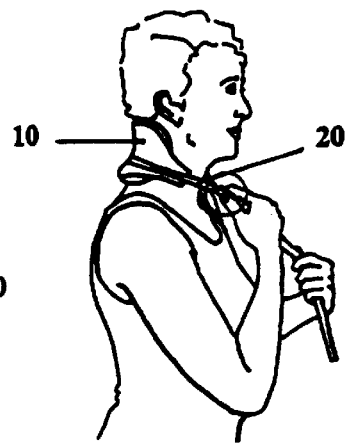
FIGURE 3a    FIGURE 3b
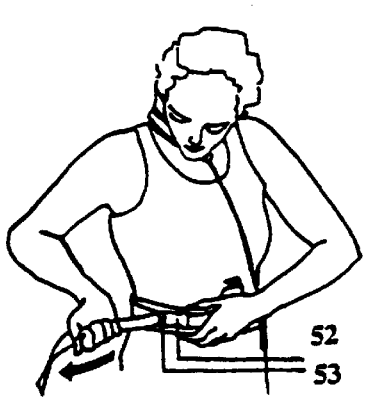 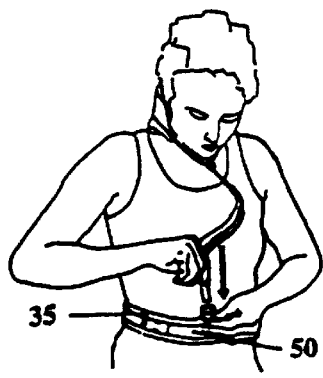 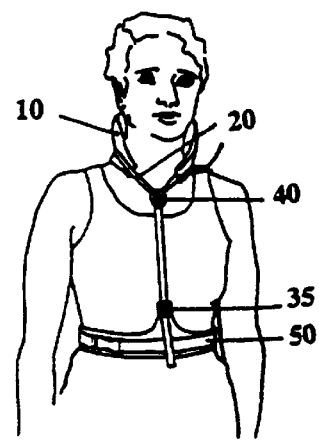
FIGURE 3c    FIGURE 3d    FIGURE 3e

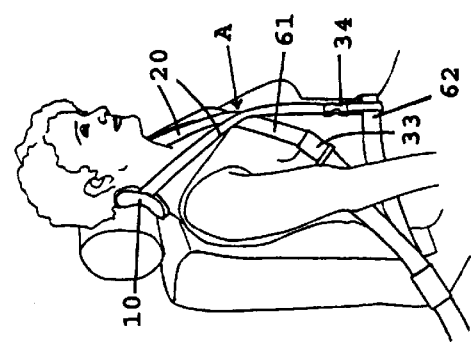
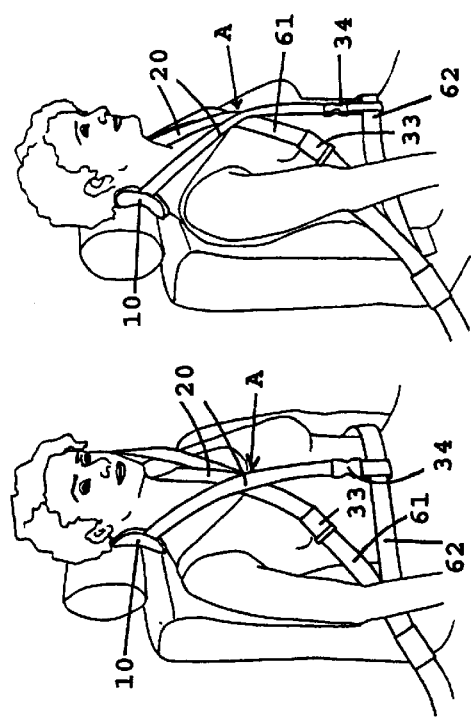
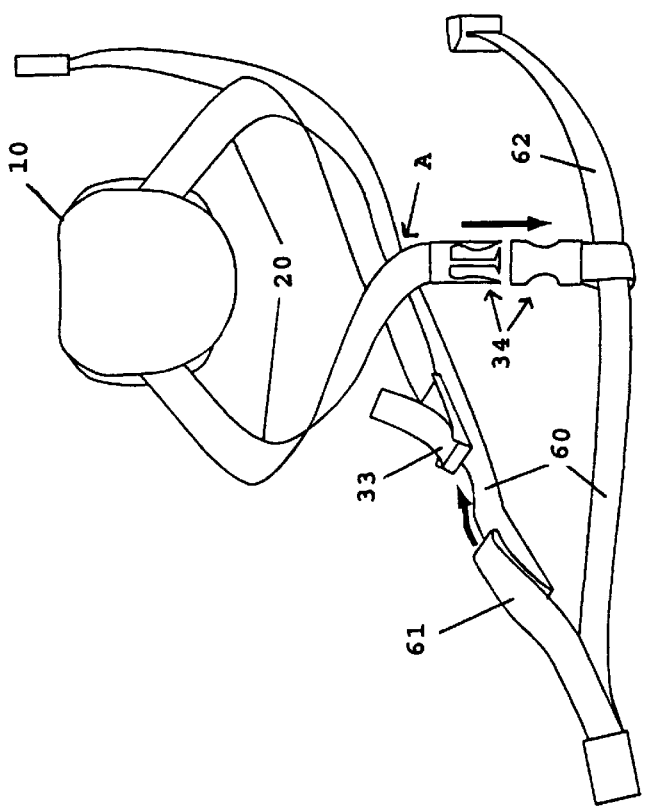

NECK SUPPORTING DEVICE

CROSS-REFERENCE TO RELATED APPLICATION

This is a continuation-in-part of application Ser. No. 09/104,502, filed Jun. 25, 1998.

BACKGROUND OF THE INVENTION

The present invention relates to a neck supporting device.

There are all kinds of situations in everyday life in which the neck of a person can suffer strain. Such a situation may, for instance, occur during a collision between cars, in which a second car collides from the rear with a first car. The passengers of the first car are then at a considerable risk of contracting so-called whiplash. Basically, the body is adjusted to move forward at approximately 5 km per hour. At a movement above 5 km/hour the neck proves to be one of the most vulnerable parts of the human body. The collision from the rear accelerates the forward movement of the car, causing the passengers who are supported by the back rest of the seats also to be accelerated forward. In nearly all cases, however, the back of the head and the neck of the passenger is not supported by the back rest or a head rest. Due to the accelerated movement forward of the torso of the person's body the head will move backward in relation to the torso.

During this event great forces are exerted on the neck and the head of the passengers. These forces can cause considerable damage to the neck and head. This damage and the ensuing complaints are called whiplash. Preventing the occurrence of whiplash can avoid much suffering, discomfort and expense.

Further, it is common practice to supply whiplash patients or patients suffering from other neck complaints with a firm, almost completely immobilizing neck collar to be worn around the throat and nape, in order to support the neck. However, this has an adverse effect on, for instance, the joints and muscles in the neck. Studies have shown that complete immobilization is not the proper treatment and that an early mobilization of the neck is very important for a successful treatment of whiplash. Another disadvantage is that such a collar is very much present. Thereby a patient's infirmity becomes obvious to his surroundings and his privacy is harmed.

Another situation in which a person's neck may be strained is when working behind a (computer) screen. This causes fatigue symptoms of the neck which after some time may lead to complaints requiring treatment. If these fatigue symptoms can be avoided, the complaints requiring treatment will also not occur.

There are neck supporting devices known, such as disclosed in U.S. Pat. No. 4,757,554, comprising a soft neck support which, in use, is held against the back of the neck by means of straps which are attached to respective ends of the neck support and run under the arm pits to the back of a wearer. However, the soft neck support does not provide a firm support to the back of the neck and the back lower part of the head, especially not when strong backward forces are involved. The neck and head are hardly prevented from moving and tilting backward with respect to the wearer's torso. Further, the neck support is not firmly and supportingly held against the back of the neck, since the straps attached to the ends of the neck support are, in use, directed to the sides of the torso. Such a configuration for the straps does also not allow for an efficient force to restrict the backward movement and tilt of the neck and the head of the wearer. Moreover, to provide some firm support, a considerable force has to be exerted on the straps, resulting in a constricting force around the chest and under the arm pits and a pressure exerted on the soft body parts of the throat, which is uncomfortable and may be harmful.

SUMMARY OF THE INVENTION

It is the object of the invention to solve the drawbacks associated with the prior art neck supporting devices. To this end the invention provides a neck supporting device comprising a neck support for supporting the back of the neck and the back lower part of the head of a wearer, said neck support including a semi-rigid member having a curvature adapted to the curvature of the back of the neck and the back lower part of the head when the head is positioned in a non-tilted position with respect to the wearer's torso, and said neck support having two ends to be positioned, in use, approximately along the sides of the neck and leaving the front of the neck uncovered; and two connecting straps for, each from a respective end of said neck support, connecting said neck support to a body harness such that, in use, said connecting straps are directed to the lower torso of the wearer.

In one preferred embodiment the neck supporting device according to the invention comprises a waist strap as the body harness, said waist strap, in use, extending at least partly and approximately around the waist of the wearer and said connecting straps being an integral part of straps adapted for, each from a respective end of said neck support, in use, crossing over each other across the chest and then across the back of the wearer, to be reciprocally fastened at least approximately on the lower torso of the wearer to simultaneously form said waist strap. For a quick and simple fastening it is preferred that the embodiment includes a coupling device for reciprocally fastening said straps.

In another preferred embodiment the neck supporting device according to the invention comprises a waist strap as the body harness, said waist strap, in use, extending at least partly and approximately around the waist of the wearer, and being a separate part of the neck supporting device, and said connecting straps being adapted for fastening to said waist strap. For a convenient fastening it is preferred that said connecting straps are adapted for fastening to said waist strap jointly, and that the neck supporting device includes a coupling device for fastening said connecting straps.

In yet another preferred embodiment of the neck supporting device according to the invention the connecting straps are adapted for fastening to a car safety belt as the body harness, one of the connecting straps being adapted for fastening, in use, to the diagonal belt of the car safety belt, and the other being adapted for fastening, in use, to the hip belt of the car safety belt. For a convenient fastening it is preferred that the neck supporting device includes coupling devices for fastening said straps to the respective belts.

In favourable embodiments the tension in the straps is variable by means of an adjustment device, so that the force by which the neck support is held against the neck, and consequently the degree of possible rearward movement of the neck, can be controlled.

In yet other embodiments the two connecting straps may be reciprocally coupled by means of a clip member which, in use, is positioned on the front of the wearer. Such a clip member further improves the stability of the neck supporting device on the body of the wearer. The clip member is preferably slidable over the straps. By sliding the clip member the course of the straps across the user can be varied as desired. In order to avoid unintended sliding of the clip member during use, it is preferable that the clip member can be secured to the straps.

It is preferred that the rear side of said neck support, in use facing away from the wearer's body, comprises said semi-rigid member and that the sides of the neck support coming into contact with the body, comprise a soft foam material. The neck support is thus able to adapt to the shape of the back of the neck and the back lower part of the head, is extremely comfortable to wear and provides yet a firm support.

It may further be advantageous that the neck support is enveloped by a covering of textile material comprising possibly towelling cotton. This material makes the feel of the neck support extremely comfortable during use and will not irritate the skin.

In a convenient embodiment the covering is in addition removable by means of closure means provided in the covering. This allows the covering surrounding the neck support to be removed for cleaning. It is also possible to use coverings of different colour and/or pattern, for instance a colour going with the clothing in order to render the device as inconspicuous as possible.

BRIEF DESCRIPTION OF THE DRAWINGS

The invention will now be elucidated with reference to the accompanying drawing in which similar parts are indicated by the same reference numbers. In the drawing:

FIG. 1 shows a first embodiment of the neck supporting device according to the invention;

FIGS. 2a, 2b and 2c show a schematic front view, side view and rear view respectively of the neck supporting device according to FIG. 1, as fitted on a user;

FIGS. 3a, 3b, 3c, 3d and 3e show a second embodiment of the neck supporting device according to the invention as fitted on a user;

FIG. 4 shows a third embodiment of the neck supporting device according to the invention;

FIGS. 5a and 5b show the third embodiment of the neck supporting device as fitted on a user; and FIG. 6 shows a schematic cross section of a neck support according to the invention.

DESCRIPTION OF PREFERRED EMBODIMENTS

Whenever the figures show the same reference numerals, they refer to the same parts.

The first embodiment of the neck supporting device according to the invention shown in FIG. 1 comprises a neck support 10 and two connecting straps 20 each attached to a different end of the neck support 10. One end of the connecting straps 20 is attached to the neck support 10 and their other end s can be reciprocally coupled by means of a coupling device 30, such as a buckle. It is also possible that the connecting straps 20 are formed by a single strap positioned around the neck support 10. This strap can be attached to the neck support at one single point, such as in the middle of the rear side, or at different points, such as at the ends. The strap could also be positioned around the neck support without being attached.

In the embodiment shown, each of the ends of the connecting straps 20 which can be reciprocally coupled, is provided with, as such known, buckle parts 31, 32 which can be coupled to form a buckle 30. It is also easy to undo this buckle 30 again. The neck supporting device according to the invention further possesses a clip member 40, reciprocally coupling the connecting straps 20 at their crossing point.

FIG. 2 shows the neck supporting device of FIG. 1 as fitted on a user. During fitting the head is passed through the opening formed by the neck support 10, the connecting straps 20 and the clip member 40. The neck support 10 is applied on the shoulders and against the neck of the user, after which the connecting straps 20 are guided over the chest, behind the back and over the belly of the user. At the belly the connecting straps 20 are coupled by means of the buckle 30. The connecting straps 20 thus also form a waist strap 50.

After coupling, the connecting straps 20 may be tightened by pulling at the end of a connecting strap 20, which connecting strap end 20 is fed through an adjustment device (not shown, but known as such), which is configured as a feed-through device and which is attached to the buckle. To allow the neck supporting device to be pulled tightly around the body, the connecting strap 20 can slide through said feed-through device in a first direction, whereas it cannot slide through in the other direction. When the buckle 30 is uncoupled, the connecting strap 20 is also able to slide in the other direction. The adjustment device may be provided at one or at both buckle parts 31, 32. A buckle with the above-mentioned adjustment device is known as such.

It is also possible to use another kind of buckle, such as a buckle which is attached to one connecting strap only and through which the other connecting strap is fed, coupling being effectuated by means of a tongue of the buckle which is inserted into an opening in the other connecting strap. The provision of a number of openings in the other connecting strap allows the neck supporting device to be fitted tighter or more loosely. However, many other embodiments of buckle couplings are feasible. It is also possible to couple the two connecting straps by means of a Velcro fastening or by means of a knot.

A second embodiment of the neck supporting device according to the invention shown in FIGS. 3a to 3e also comprises a neck support 10 and a strap positioned around the neck support 10, which strap is attached (not shown) to the ends and the rear middle of the neck support 10. This results in two connecting straps 20, each being attached to a different end of the neck support 10. In the embodiment shown, said connecting straps 20 are fed through a clip member 40. The neck support 10 with the connecting straps 20 and the clip member 40 according to the second embodiment, are fitted on a user in a similar manner as in the first embodiment.

In the application of this embodiment as shown in FIG. 3e the ends of the connecting straps 20 facing away from the neck support 10, are attached to a waist strap 50 by means of a coupling device 35. This coupling device 35 may be a buckle, but is in the embodiment shown configured as a feed-through device, which also serves as an adjustment device by which the two connecting straps 20 may be tightened between the neck support 10 and the waist strap 50. The two connecting straps 20 extend, bundled together, between the clip member 40 and the waist strap 50.

The waist strap 50 may be a trouser belt to which a (part of a) coupling device for the connecting straps 20 is attached. In the embodiment shown in FIGS. 3a to 3e the waist strap 50 is formed by a strap having two ends which can be coupled by means of a buckle 52. To the buckle 52 an adjustment device 53, which is configured as a feed-through device, is attached for tightening the waist strap 50.

The clip member 40 through which the two connecting straps 20 are fed, can slide over the connecting straps 20 of the two embodiments shown. This slidable clip member 40 allows adjustment of the course of the connecting straps 20 over the chest or belly of the user. The more the clip member 40 is slid toward the neck support 10, the firmer the neck support will fit around the neck of the user. The position of the clip member 40 may be varied as required. In order to keep the clip member 40 in a chosen position on the connecting straps 20, it may be secured on the connecting straps 20 by means which are not shown.

A third embodiment of the neck supporting device according to the invention is shown in FIG. 4. The third embodiment also comprises a neck support 10 and a strap positioned around the neck support 10, which strap is attached (not shown) to the ends of the neck support 10. This again results in two connecting straps 20, each being attached to a different end of the neck support 10.

In the third embodiment the ends of the connecting straps 20 facing away from the neck support 10 are adapted for fastening to a car safety belt 60. Such application is of course also feasible for other situations, such as use in speedboats, golf-trolleys, funcars, hydrofoils, etc. One of the connecting straps 20 includes a coupling device, such as a buckle 33, for fastening, in use, to the diagonal belt 61 of the car safety belt. The second connecting strap 20 is adapted for fastening to the hip belt 62 of the car safety belt with for instance a buckle 34. Both connecting straps 20, in use, cross each other as indicated with arrow A across the chest. They may be reciprocally coupled on the front of the wearer by a clip member as in the previous embodiments. Such a clip member is, however, not included in the embodiment shown. Further, the second connecting strap 20 may also be adapted for fastening to the diagonal belt, and both connecting straps 20 may be adapted for fastening to the diagonal belt jointly.

As in the previous embodiments the connecting straps 20 may include an adjustment device for tightening the connecting straps 20 to firmly hold the neck support 10 against the neck of the user and prevent the neck and head of the wearer from moving or tilting backwards.

FIG. 6 shows a possible schematic cross section of the neck support 10 according to the invention.

The shape of the neck support 10 is adapted to that of the neck, the shoulders and the head, as can be seen in FIG. 2, 3 and 5, and the front-, upper- and underside coming into contact with the body, are made from a soft foam material 110, as shown schematically in FIG. 6. The rear side of the neck support 10 comprises a semi-rigid member 120 the curvature of which is adapted to the back of the neck and the back of the head, ensuring that the neck support 10 provides optimal support.

The neck support 10 may be enveloped by a material layer 140 of a textile material such as towelling with a pleasant feel to the skin. In a possible embodiment said second layer 140 is provided with a closure means 150, such as for instance a zipper, to allow the layer to be removed and changed. This makes it possible to clean the second layer 140 and to choose the second layer 140 in a colour and pattern to go with the clothing of the user.

The embodiments of the neck supporting device according to the invention shown can be fitted on the body of a user easily and within a few seconds. In addition, they can be adjusted to the individual user.

A major advantage of the neck supporting device according to the invention is the great degree of freedom of movement, restricting everyday activities as little as possible and supporting the neck in the correct manner to ensure a successful treatment of whiplash. In addition, said neck supporting device is virtually inconspicuous and may be disguised completely, for instance, by wearing a shawl.

The neck supporting device according to the invention affords excellent protection against incidents in which straining of the head and neck may occur, such as in a car collision from the rear (whiplash). The device may be applied as preventive means against injury of this kind, but also as a support for people suffering from existing neck complaints stemming, for instance, from a whiplash and other strains, from a neck hernia or a neck sprain, after a neck hernia operation, for the treatment of neck injury and degeneration (arthrosis), etc.

The embodiments describe above are not to be understood as limiting the invention. The neck supporting device may be realized in a variety of embodiments, all deemed to be within the scope of the appended claims.

What is claimed is:

1. A neck supporting device comprising a neck support for supporting the back of the neck and the back lower part of the head of a wearer, said neck support including a semi-rigid member having a curvature adapted to the curvature of the back of the neck and the back lower part of the head when the head is positioned in a non-tilted position with respect to the wearer's torso, and said neck support having two ends to be positioned, in use, approximately along the sides of the neck and leaving the front of the neck uncovered; and two connecting straps for, each from a respective end of said neck support, connecting said neck support to a body harness such that, in use, said connecting straps are directed to the lower torso of the wearer.

2. A neck supporting device according to claim 1, further comprising a waist strap as the body harness, said waist strap, in use, extending at least partly and approximately around the waist of the wearer.

3. A neck supporting device according to claim 2, wherein said connecting straps are an integral part of straps adapted for, each from a respective end of said neck support, in use, crossing over each other across the chest and then across the back of the wearer, to be reciprocally fastened at least approximately on the lower torso of the wearer to simultaneously form said waist strap.

4. A neck supporting device according to claim 3, including a coupling device for reciprocally fastening said straps.

5. A neck supporting device according to claim 3, including an adjustment device for controlling the tension in said straps when fastened.

6. A neck supporting device according to claim 3, including a clip member for reciprocally coupling said straps such that said clip member, in use, is positioned on the front of the wearer.

7. A neck supporting device according to claim 6, wherein said clip member is slidable over said straps.

8. A neck supporting device according to claim 7, wherein said clip member is securable to said straps.

9. A neck supporting device according to claim 2, wherein said waist strap is a separate part of the neck supporting device, and said connecting straps are adapted for fastening to said waist strap.

10. A neck supporting device according to claim 9, wherein said connecting straps are adapted for fastening to said waist strap jointly.

11. A neck supporting device according to claim 9, including a coupling device for fastening said connecting straps.

12. A neck supporting device according to claim 9, including an adjustment device for controlling the tension in said connecting straps when fastened.

13. A neck supporting device according to claim 9, including a clip member for reciprocally coupling said connecting straps such that said clip member, in use, is positioned on the front of the wearer.

14. A neck supporting device according to claim 13, wherein said clip member is slidable over said connecting straps.

15. A neck supporting device according to claim 14, wherein said clip member is securable to said connecting straps.

16. A neck supporting device according to claim 1, wherein said connecting straps are adapted for fastening to a safety belt as the body harness.

17. A neck supporting device according to claim 16, wherein a first one of the connecting straps is adapted for fastening, in use, to the diagonal belt of the safety belt.

18. A neck supporting device according to claim 17, including a coupling device for fastening said first connecting strap to the diagonal belt.

19. A neck supporting device according to claim 16, wherein a second one of the connecting straps is adapted for fastening, in use, to the hip belt of the safety belt.

20. A neck supporting device according to claim 19, including a coupling device for fastening said second connecting strap to the hip belt.

21. A neck supporting device according to claim 16, including an adjustment device for controlling the tension in said connecting straps when fastened.

22. A neck supporting device according to claim 16, including a clip member for reciprocally coupling the connecting straps such that said clip member, in use, is positioned on the front of the wearer.

23. A neck supporting device according to claim 22, wherein said clip member is slidable over said connecting straps.

24. A neck supporting device according to claim 23, wherein said clip member is securable to said connecting straps.

25. A neck supporting device according to claim 1, wherein the rear side of said neck support, in use facing away from the wearer's body, comprises said semi-rigid member.

26. A neck supporting device according to claim 1, wherein the sides of said neck support coming into contact with the wearer's body comprise a soft foam material.

27. A neck supporting device according to claim 1, wherein said neck support is enveloped by a covering of textile material.

28. A neck supporting device according to claim 1, wherein said textile material comprises towelling cotton.

29. A neck supporting device according to claim 1, wherein said covering is removable by means of closure means provided in said covering.

30. A neck supporting device comprising a neck support for supporting the back of the neck and the back lower part of the head of a wearer, said neck support including a semi-rigid member having a curvature adapted to the curvature of the back of the neck and the back lower part of the head when the head is positioned in a non-tilted position with respect to the wearer's torso, and said neck support having two ends to be positioned, in use, approximately along the sides of the neck and leaving the front of the neck uncovered; and two straps adapted for, each from a respective end of said neck support, in use, crossing over each other across the chest and then across the back of the wearer, to be reciprocally fastened at least approximately on the lower torso of the wearer to simultaneously form a waist strap, said waist strap, in use, extending at least partly and approximately around the waist of the wearer.

31. A neck supporting device comprising a neck support for supporting the back of the neck and the back lower part of the head of a wearer, said neck support including a semi-rigid member having a curvature adapted to the curvature of the back of the neck and the back lower part of the head when the head is positioned in a non-tilted position with respect to the wearer's torso, and said neck support having two ends to be positioned, in use, approximately along the sides of the neck and leaving the front of the neck uncovered; a waist strap, in use, extending at least partly and approximately around the waist of the wearer; and two connecting straps adapted for, each from a respective end of said neck support, fastening to said waist strap.

32. A neck supporting device comprising a neck support for supporting the back of the neck and the back lower part of the head of a wearer, said neck support including a semi-rigid member having a curvature adapted to the curvature of the back of the neck and the back lower part of the head when the head is positioned in a non-tilted position with respect to the wearer's torso, and said neck support having two ends to be positioned, in use, approximately along the sides of the neck and leaving the front of the neck uncovered; and two connecting straps adapted for, each from a respective end of said neck support, fastening to a car safety belt, one of the connecting straps being adapted for fastening to the diagonal belt and the other being adapted for fastening to the hip belt of the car safety belt.

\* \* \* \* \*